(12) United States Patent
Kenny et al.

(10) Patent No.: US 6,186,012 B1
(45) Date of Patent: Feb. 13, 2001

(54) HAND HELD SAMPLE TUBE MANIPULATOR, SYSTEM AND METHOD

(75) Inventors: Donald V. Kenny; Deborah L. Smith, both of Liberty Township; Richard A. Severance, deceased, late of Columbus, all of OH (US), by Vilora E. Severance, legal representative

(73) Assignee: Battelle Memorial Institute, Columbus, OH (US)

( * ) Notice: Under 35 U.S.C. 154(b), the term of this patent shall be extended for 0 days.

(21) Appl. No.: 09/222,627

(22) Filed: Dec. 29, 1998

Related U.S. Application Data

(60) Provisional application No. 60/070,025, filed on Dec. 30, 1997.

(51) Int. Cl.$^7$ .................................................. G01N 1/00
(52) U.S. Cl. ...................................................... 73/863.12
(58) Field of Search ......................... 73/864.23, 864.24, 73/864.14, 863.11, 863.12, 863.21, 864.81, 864.85; 422/63, 84, 88, 100

(56) References Cited

U.S. PATENT DOCUMENTS

| | | | |
|---|---|---|---|
| 2,959,964 | * 11/1960 | Streitfeld | 73/864.14 |
| 3,246,559 | 4/1966 | Clifford, Jr. . | |
| 3,471,692 | 10/1969 | Llewellyn et al. . | |
| 4,046,014 | * 9/1977 | Boehringer et al. | 73/863.12 |
| 4,170,901 | * 10/1979 | Conkle et al. | 73/863.12 |
| 4,283,950 | 8/1981 | Tervamäki . | |
| 4,350,037 | 9/1982 | Higham . | |
| 4,474,071 | 10/1984 | d'Autry . | |
| 4,478,095 | * 10/1984 | Bradley et al. | 73/864.23 |
| 4,541,268 | 9/1985 | Ordernheimer . | |
| 4,616,514 | 10/1986 | Magnussen, Jr. et al. . | |
| 4,732,046 | * 3/1988 | Lawrence et al. | 73/863.12 |
| 4,735,905 | 4/1988 | Parker . | |
| 4,747,831 | 5/1988 | Kulli . | |
| 4,849,179 | 7/1989 | Reinhardt et al. . | |
| 4,869,117 | 9/1989 | McAndless et al. . | |
| 5,065,614 | 11/1991 | Hartman et al. . | |
| 5,092,219 | * 3/1992 | Rounbehler et al. | 73/863.12 |
| 5,098,388 | 3/1992 | Kulkashi et al. . | |
| 5,104,625 | * 4/1992 | Kenney | 73/864.14 |
| 5,114,342 | 5/1992 | Young et al. . | |
| 5,123,276 | 6/1992 | Hartman et al. . | |
| 5,172,581 | 12/1992 | Brackmann et al. . | |
| 5,195,325 | 3/1993 | Short et al. . | |
| 5,219,198 | 6/1993 | Davis . | |
| 5,257,527 | 11/1993 | Kingsbury . | |
| 5,425,921 | 6/1995 | Coakley et al. . | |

FOREIGN PATENT DOCUMENTS 0 292 844   7/1992   (EP) .

OTHER PUBLICATIONS

Scientific Instrument Services Inc.; 1992–1993 Catalog; pp. 1,2,5,6,8,10–13,16,18,27,34.

\* cited by examiner

Primary Examiner—Robert Raevis
(74) Attorney, Agent, or Firm—Klaus H. Wiesmann

(57) ABSTRACT

A manipulator apparatus, system and method for measuring analytes present in sample tubes. The manipulator apparatus includes a housing having a central bore with an inlet end and outlet end; a plunger mechanism with at least a portion thereof slideably disposed for reciprocal movement within the central bore, the plunger mechanism having a tubular gas channel with an inlet end and an outlet end, the gas channel inlet end disposed in the same direction as said inlet end of the central bore, wherein the inlet end of said plunger mechanism is adapted for movement so as to expel a sample tube inserted in the bore at the outlet end of the housing, the inlet end of the plunger mechanism is adapted for connection to gas supply; a first seal is disposed in the housing for sealing between the central bore and the plunger mechanism; a second seal is disposed at the outlet end of the housing for sealing between the central bore and a sample tube; a holder mounted on the housing for holding the sample tube; and a biasing mechanism for returning the plunger mechanism to a starting position.

16 Claims, 9 Drawing Sheets

HAND HELD SAMPLE TUBE MANIPULATOR, SYSTEM AND METHOD

This application claims the benefits of U.S. Provisional Application Ser. No. 60/070,025 filed Dec. 30, 1997, having the same title as the present application, the disclosure of which is incorporated as if fully rewritten herein.

The United States Government has rights in this invention pursuant to a contract with the U.S. Department of Energy under Contract No. DE-AC06-76RL01830.

FIELD OF THE INVENTION

The invention discloses a hand held device used to manipulate thermal desorption type sample tubes containing analytes. For example, air/gas samples are collected in the sample tubes. Sample tubes are manipulated with the inventive apparatus, moved from sample trays or stations into a heating area where analytes are desorbed from the sample tube and introduced into a measuring device. In another embodiment the invention encompasses the hand held sample tube manipulator as part of a system for introducing analytes from sample tubes into a measuring device.

BACKGROUND OF THE INVENTION

The sample desorption process where analytes are desorbed from sample tubes and moved into a measuring apparatus involves time consuming steps. The invention reduces the time and manipulative steps necessary for putting samples into measuring apparatus. In gathering samples such as for example environmental monitoring, it is not unusual to have several hundred sample tubes collected from one or more monitoring sites. The manipulation of these sample tubes typically involves removal from a sample tray, insertion into a measuring apparatus, measurement, removal and storage or disposal.

As can easily be seen these steps are time consuming particularly when the number of sample tubes is very large. Thus if two hundred tubes are to be measured, a time savings of only 1 minute per tube can result in time savings of 200 minutes or 3⅓ hours. In a typical days work it would not be unusual to measure even more tubes than the aforementioned 200. The present invention fulfills the need for reducing the time need for sample measurement.

BRIEF DESCRIPTION OF THE INVENTION

Broadly, the invention discloses apparatus, systems, methods and uses for the efficient manipulation of sample tubes. The invention reduces the time required for manipulation of sample tubes by apparatus that allows the combination of sample tube manipulation steps that heretofore were performed separately. One aspect the invention typically includes apparatus such as a hand held sample tube desorber and ejector. In another aspect the invention typically includes a system for manipulating and desorbing sample tubes. In yet another aspect the invention typically includes a method for the manipulation of hand held sample desorption tubes. In another aspect of the invention, the invention typically includes a method for operating a system for manipulating and analyzing sample tubes with apparatus such as a gas chromatograph or mass spectrometer. In another aspect of the invention, the invention encompasses a system for sample collection and introduction into a measuring device.

Typically one aspect of the invention includes a sample tube manipulator including: a housing having a central bore with an inlet end and outlet end; a plunger mechanism at least a portion of which is tubular and is slideably disposed within the central bore for reciprocal movement therein. The tubular portion typically is used to expel a sample tube inserted in the central bore at its outlet end, the tubular portion also serving as a gas channel with an inlet end and an outlet end disposed in the same direction as the inlet and outlet end of the central bore. The inlet end of the movable plunger mechanism is typically provided for connection to a gas supply and/or a vacuum pump. Also included is a first seal disposed in the housing for sealing between the central bore and the moveable plunger mechanism; a second seal disposed at the outlet of the housing adapted for sealing between the central bore and an inserted sample tube. Includes also is a holder mounted on the housing adapted to hold the sample tube while allowing ejection of the sample tubes when the plunger mechanism moves reciprocally. A biasing mechanism is used for returning the plunger mechanism to a starting position after movement of the plunger. Typically the plunger mechanism includes a plunger head adapted for movement by manual depression, or a solenoid or pneumatic mechanism that provides movement. Typically the plunger mechanism comprises the reciprocally moveable portion and a stationary portion disposed on the housing for powering the reciprocally moveable portion. The stationary portion typically comprises a stationary portion of a solenoid, pneumatic mechanism, motor, lever, or may comprise a portion of a hand or glove.

Another aspect of the invention provides for a sample tube manipulator including: a housing having a central bore having an upper and a lower end; a plunger mechanism having a tubular portion slideably disposed in the upper end of the bore for reciprocal movement in the bore, the plunger mechanism having a gas channel between upper and lower ends, the upper end of the plunger mechanism adapted to power the plunger mechanism, the lower end of the tubular portion of the plunger mechanism adapted to mate with a sample tube inserted in the lower central bore end for providing gas flow from the gas channel to the sample tube, the plunger mechanism adapted to expel a sample tube inserted in the lower end of the central bore when the plunger mechanism moves; a first gas seal disposed in the central bore, between the bore and the tubular portion of the plunger, that provides gas sealing in the space between the tubular portion of the plunger mechanism and the central bore; a second gas seal disposed at the lower portion of the housing, that provides gas sealing around the outer circumference of an inserted sample tube; a tube holder disposed at the lower portion of the housing, adapted to hold a sample tube inserted in the lower portion of the housing; a biasing mechanism disposed at the upper end of the housing adapted to return the plunger mechanism to a starting position after movement of the plunger mechanism. Typically the plunger mechanism includes a plunger head adapted for movement by manual depression, or a solenoid or pneumatic mechanism that provides movement. Typically the plunger mechanism comprises a reciprocally moveable portion and a stationary portion disposed on the housing for powering the reciprocally moveable portion. The stationary portion typically comprises a stationary portion of a solenoid, pneumatic mechanism, motor, lever, or may comprise a portion of a hand or glove.

A further embodiment of the invention includes: a sample tube manipulator with a housing having a central bore with an upper and a lower end; a plunger mechanism having a tubular portion disposed in the upper end of the bore for reciprocal movement in the bore, the plunger mechanism having a gas channel between and upper and lower ends, the upper end of the plunger mechanism enlarged to a plunger head, the lower end of the tubular portion of the plunger mechanism is adapted to mate with a sample tube inserted in the lower central bore end for providing gas flow from the gas channel to the sample tube, the plunger mechanism is adapted to expel a sample tube inserted in the lower end of the central bore when the plunger head is depressed; a first sealing mechanism disposed in the central bore, between the bore and the tubular portion of the plunger, that provides gas sealing in the space between the tubular portion of the plunger mechanism and the central bore; a second sealing mechanism disposed at the lower portion of the housing, that provides gas sealing around the outer circumference of an inserted sample tube; a holding mechanism disposed at the lower portion of the housing that is adapted to hold a sample tube inserted in the lower portion of the housing; and a biasing mechanism disposed at the upper end of the housing that returns the plunger mechanism to a starting position after depression of the plunger.

A still further embodiment of the invention includes a system for measuring analytes present in a sample tube that includes: a source of gas; first gas control connected to the gas source, that is adapted to receive and regulate gas from the gas source; sample tube manipulator for moving and handling a sample tube, that is operationally connected to the first gas control, the sample tube manipulator is adapted to: receive and hold the sample tube, seal one end of the sample tube from the environment, and provide a flow of gas received from the first gas control to the sample tube; a heater that is adapted to heat the sample tube while the sample tube is held by the sample tube manipulator; sealing and gas receiver for sealing the other end of the sample tube from the environment and for receiving gas flow from the sample tube; and second gas control that is adapted for receiving gas from the sealing and gas receiver and regulating the gas flow. Typically the system includes a measuring device connected to the second gas controller, for measuring analytes present in gas received from the second gas control. The measuring device is typically a gas chromatograph or mass spectrometer.

A yet further embodiment of the invention includes a system for measuring analytes present in a sample tube that includes a source of gas; a vacuum pump; first gas control (1) connected to the gas source, and adapted to receive and regulate gas from the gas source, and (2) connected to the vacuum pump for regulation gas flow to or from the vacuum pump; sample tube manipulator for moving and handling a sample tube, operationally connected to the gas control, the sample tube manipulator is adapted to: receive and hold the sample tube, to seal one end of the sample tube from the environment, and to provide a flow of gas to or from the first gas control to or from the sample tube; a heater is used to heat the sample tube while the sample tube is held by the sample tube manipulator; a sealing and gas receiving mechanism seals the other end of the sample tube from the environment and receives gas flow from the sample tube; a second gas control adapted for receiving gas from the sealing and gas receiving mechanism and regulating the gas flow. Typically the system also includes a measuring device connected to the second gas control mechanism, for measuring analytes present in gas received from the second gas control mechanism. Typically the measuring device is a gas chromatograph.

A still further embodiment of the invention includes a method for measuring analytes present in a sample tube by the steps of: inserting one end of the sample tube in the sample tube manipulator described above, mating the sample tube with a gas sealing and receiving mechanism adapted to seal the other end of the sample tube from the environment; heating the sample tube in a manner adapted to desorb analytes present in the sample tube; providing a flow of gas to sweep the analytes from the sample tube; and directing the gas flow from the gas sealing and receiving mechanism to a measuring device and measuring for the presence of selected analytes. The heating described above must, of course, be at or above a temperature where the analytes are released from the sorbent.

DETAILED DESCRIPTION OF THE INVENTION AND BEST MODE

Figure 1:
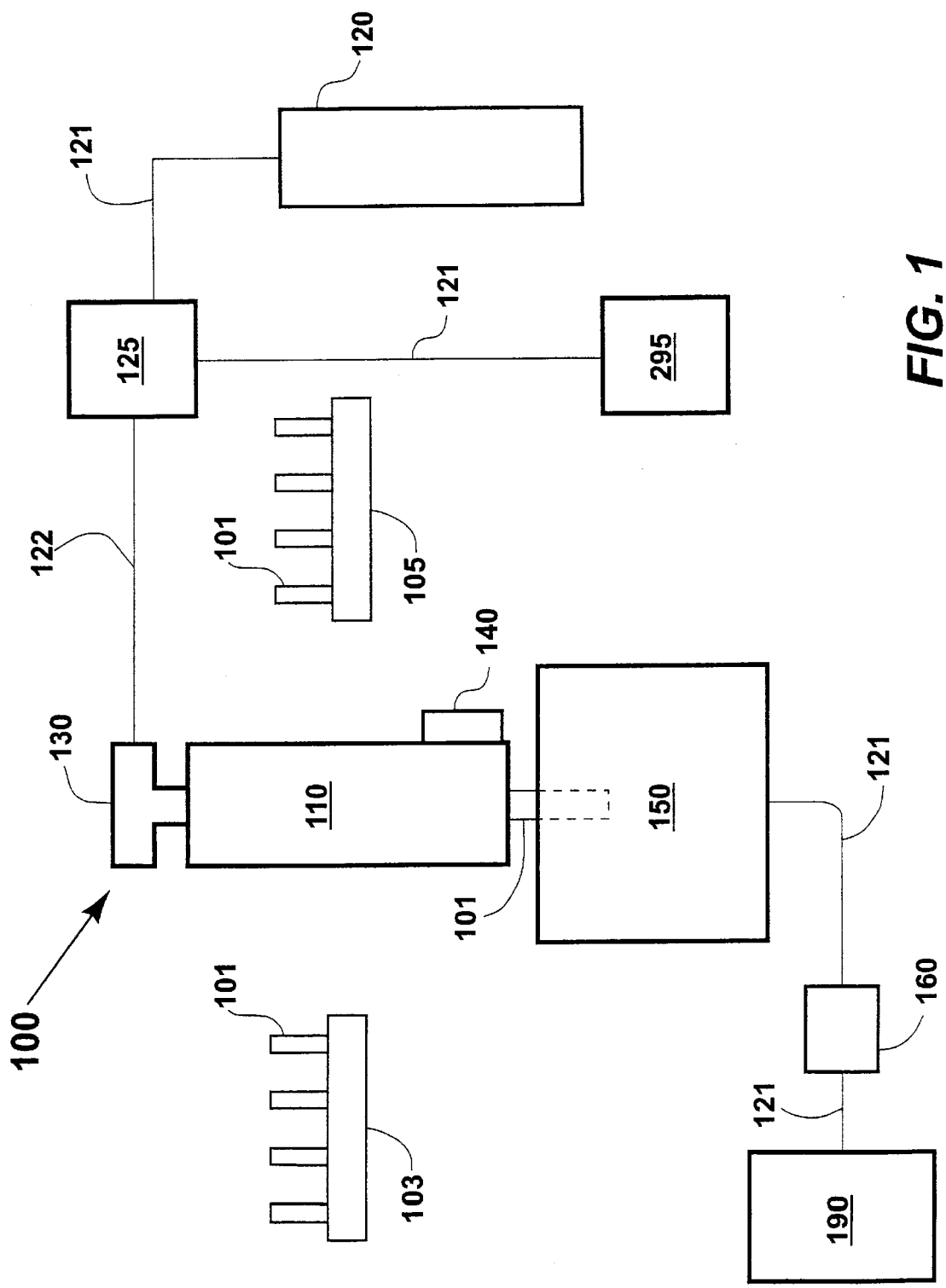
FIG. 1 is an overall schematic of the chemical sensor system 100 of which the sample tube manipulator 110 is a part.

Broadly the invention involves apparatus and methods for the efficient manipulation of sample tubes. Manipulation in the context of this application includes some or all of the procedural steps outlined below:

- sample tube removal from a first site such as a first storage tray;
- sample tube transport;
- sample tube placement into a desorption device;
- closing and sealing of the desorption device;
- desorption of the sample tube
- opening of the desorption device;
- sample tube removal from the desorption device;
- sample tube transport back to the first site or to a second site such as a second storage tray; and
- sample tube placement in the first site or in a second site.

The invention solves the problem of reducing the time required for manipulation of sample tubes by combining operations that heretofore were performed as separate steps. For example, in the step of removing the sample tube from a first site, one end of the tube is automatically connected into the gas flow supply for desorption and that end of the tube is also sealed to the outside environment. When the other end of the sample tube is inserted into the remainder of the system, the sample tube is automatically connected to the rest of the desorption measurement system including receiving gas flow lines, that end of the sample tube is then automatically sealed from the environment, and (if desired) a heater is automatically activated. These combined steps greatly reduce the time needed for measuring large quantities of sample tubes. In addition, possibility of contamination of the tube is reduced because of the fewer manipulative steps involved.

Alternative embodiments for the device are discussed here briefly and in detail below. Broadly the invention discloses several means and mechanisms for depression of the tube 215 for expulsion of sample tube 101. Thus the general terms plunger means or plunger mechanism typically can include the specific mechanism of plunger mechanism 130 (FIG. 3A) or other embodiments for actuating or reciprocating tube 215 such as solenoid mechanism 300 (FIG. 3B) or pneumatic mechanism 400 (FIG. 3C). Plunger mechanism 130 is typically wholly mounted on tube 215 while movable portions of solenoid mechanism 300 and pneumatic mechanism 400 are mounted on the tube 215 and stationary portions thereof are typically mounted on the housing 210. Plunger mechanism 130 is typically wholly mounted on tube 215 because in this embodiment the hand is used to depress the plunger head 220. The palm of the hand typically grips the housing 210 and a thumb is used to depress plunger head 220. Thus the hand spans the gap between the housing 210 and plunger mechanism 130 and provides the necessary push points even with all of plunger mechanism 130 mounted on tube 215. In this sense the hand provides the necessary stationary part of the plunger means that is located on the housing in the other typical embodiments.

Referring now to FIG. 1, one aspect of the invention includes a system 100 for manipulation, desorption, and measurement of material in a sample tube 101. Sample tube 101 is typically picked up with manipulator 110 from a first site 103, placed in a heater/desorber 150, and moved back to site 103 or to a separate site 105 reserved for desorbed sample tubes 101. During desorption sample tube 101 is heated to a temperature required to desorb analytes of interest. A flow of gas from a gas supply 120 flows via gas lines 121,122 through a controller mechanism 125 to manipulator 110, through sample tube 101. Sample tube 101 is held in place by holding mechanism 140 and its lower end is now inserted in heater 150. The flow of gas pushes gases, evolved during desorption of sample, through gas lines 121, to a second controller mechanism 160 and thence to measurement device 190. Gas line 122 is typically flexible so as to allow movement of the manipulator. Typically flexible gas line 122 is connected to manipulator 110 at plunger mechanism 130.

In an alternate optional embodiment the system 100 includes a vacuum pump 295 and additional gas line 121 that connects it to control mechanism 125. This embodiment allows the use of the system 100 as a sampler. During use in the sampling mode, system 100 will have the gas supply 120 turned off, preferably after the system has been flushed with inert gas. The operator will then insert a sample tube 101 into manipulator 110 in the same manner as if a desorption were to be performed. However, the operator will then place the manipulator into the area to be sampled rather than into the heater 150, or simply hold the sample tube in place or carry it throughout the area to be measured until the measurement is done. When vacuum pump 295 is turned on, ambient air is drawn into the sample tube 101, then through the manipulator 110 to control mechanism 125 and then to the vacuum pump 295. Chemicals of interest, that are present in the air, will be taken up by sorption material in sample tube 101. As many measurements as desired can be made, at which time the system 100 can be switched back to a desorption and measurement mode.

Figure 2:
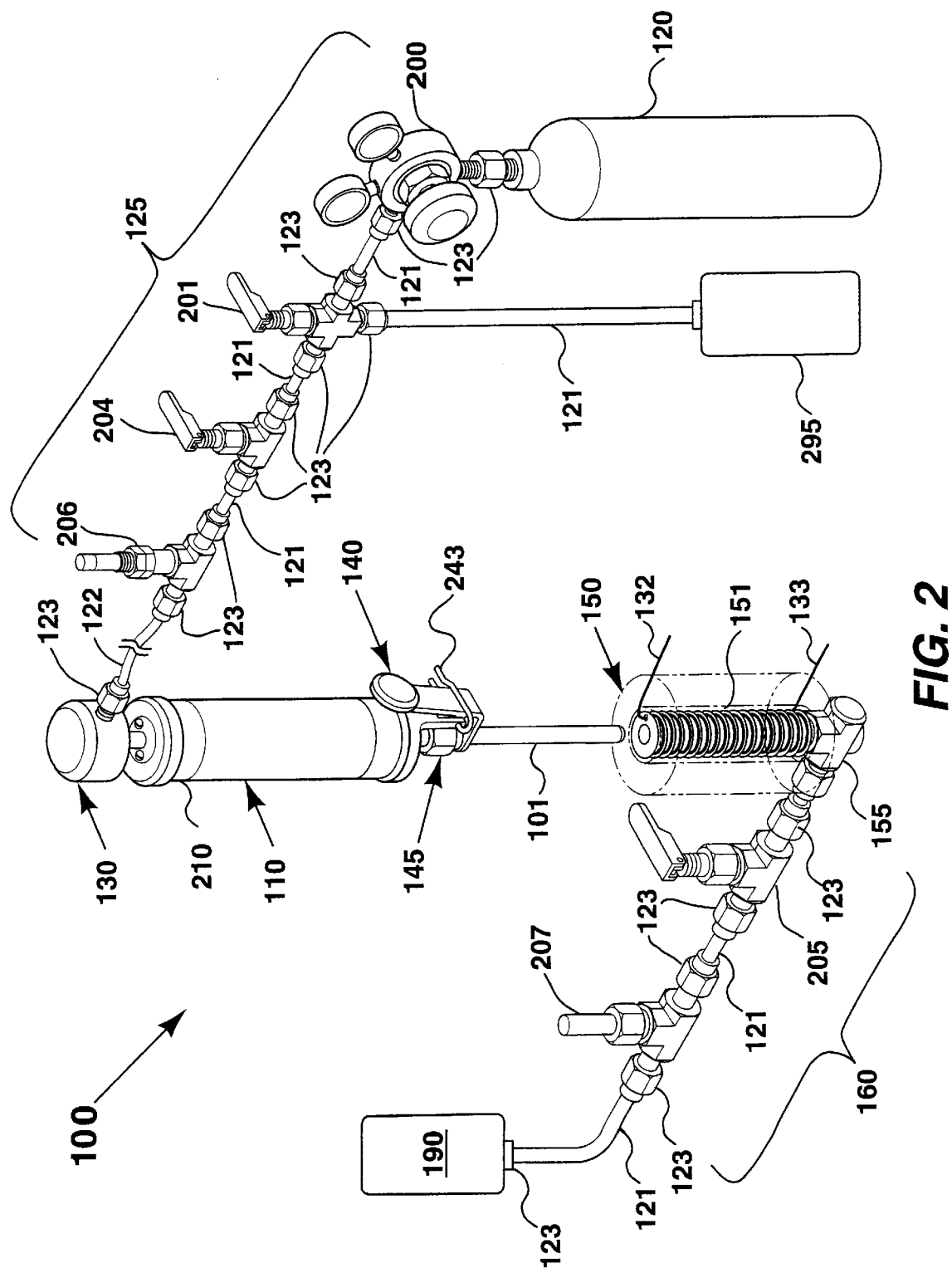
FIG. 2 shows a more detailed view of the chemical sensor system 100.

Referring now to FIG. 2, which shows a preferred embodiment of the invention, gas cylinder 120, that typically supplies an inert gas (e.g. helium, nitrogen, argon alone or as a mixture of gases) is connected to the sample tube manipulator 110 via control mechanism 125 and flexible gas line 122. Control mechanism 125 in this embodiment comprises pressure regulator 200, gas lines 121 (typical), two-way valve 201, on-off valve 20A and needle valve 206. Typically gas lines 121,122 and various parts of the system 100 have appropriate fittings 123 for connection to valves, regulators, measuring devices and other components of the system 100.

Regulator 200, two-way valve 201, on-off valve 204 and needle valve 206 control gas flow from the gas cylinder 120. Two way valve 201 controls flow of gases from gas cylinder 120 and to vacuum pump 295, it is configured to provide flow from or to one of these at a time. A sample tube 101 is shown inserted in the bottom of the sample tube manipulator 110 that is held in place by holding mechanism 140. A lower sealing mechanism 145 that may be a part of or separate from holding mechanism 140 prevents gas leakage. Typically a swagelock/O-ring fitting is used for sealing. If desired, other means known in the art for appropriately controlling a flow of gas, both electronic and manual, can be used.

A flow of inert gas through the sample tube manipulator 110 is started to remove the residual air/oxygen from the sample tube 101. After a few moments the sample tube 101 is placed into a heated block 150. Block 150 is typically heated electrically with an electric heating unit 151 that surrounds block 150 via electrical leads 132,133. While electrical heating is illustrated here other hearing means known in the art may be used. Microwave, resistance, infrared, chemical and other forms of heating may all be used. The outlet gas receiving connection, with which sample tube 101 mates and that acts as a gas receiver for gas flow from the sample tube, in this case an elbow 155, is preferably also sealed with a swagelock/O-ring connector 260. Desorbed gases flow from the sample tube 101 in the heater 150 via elbow 155 to a second on/off valve 205 and needle valve 207 and thence via gas line 121 to measuring device 190. The heating block is preferably a resistance type heater and is configured to open and close for ease of insertion and seating of sample tube 101. The heating block 150 is shown in the closed position during the heating part of the procedure.

By the process of heating, analytes on the sorbent of sample tube 101 are desorbed and held in place in the gaseous state until the second on/off valve 205 at the end of the heating block 150 is opened (second controller mechanism). Once the second on/off valve 205 is opened the analytes are "pushed" into the sampling stream of a measuring device 190 such as a mass spectrometer. After the analysis is complete, the second on/off valve 205 is closed, the sample tube manipulator 110 is used to remove the sample tube 101 from the heating block 150. Upon removal from the heating block 150, sample tube 101 is still very hot. The removal of the tube is facilitated by thumb depression of the plunger head 220. Depression of the plunger head 220 moves tube 215 downward and ejects the sample tube 101 from the sample tube manipulator 110.

In an effort to simplify a workers hand manipulation a design similar to an automatic pipetor is used. The device is designed so that it can be used by both laboratory and field workers and involves the least amount of hand manipulations, yet assures good analytical measurements. It would be unacceptable to require a worker, for example, to remove his or her sampler, attach a swagelock connector, tighten both ends with wrenches, place it in a heating device, and then repeat the procedure in reverse with the hot sampling tube.

Figure 3A:
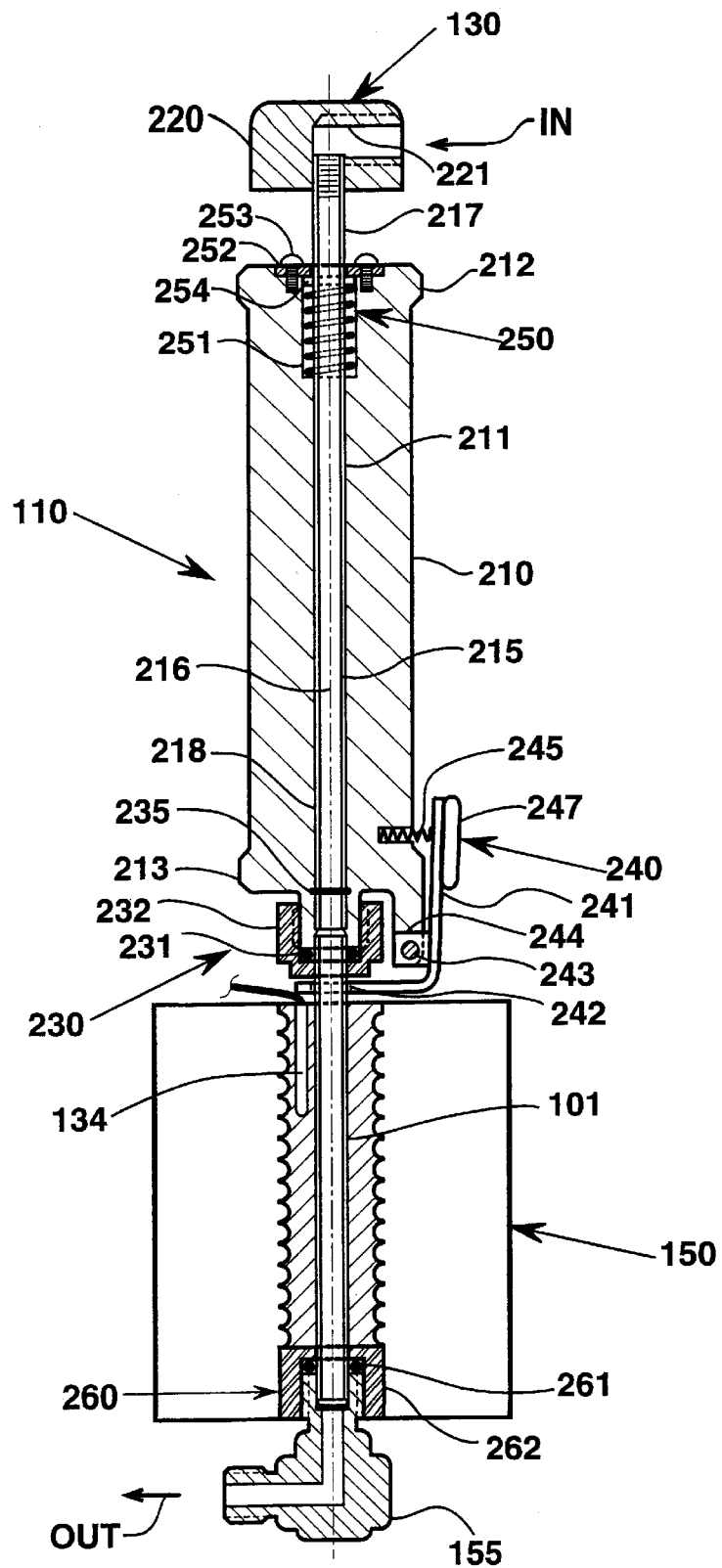
FIG. 3A is a cutaway view of the hand held sample tube manipulator 110 configured so as to expel a sample tube 101 by manual depression of a plunger mechanism 130.

Referring now to FIG. 3A, which shows the sample tube manipulator 110 inserted in the heating block 150. Sample tube manipulator 110 is provided with an elongate housing 210 having a bore 211 therethrough and having an upper end 212 and lower end 213. Plunger mechanism 130 typically comprises a tube 215 with a gas channel 216 having an upper inlet end 217 and a lower outlet end 218. The upper inlet end of plunger mechanism 130 is enlarged to form a plunger head 220 to facilitate depression of the plunger mechanism 130 by finger, thumb or hand movement. Plunger mechanism 130 may be formed of separate parts as shown in FIG. 3, or may be formed as an integral unit by processes known in the art. The tube 215 of plunger mechanism 130 is disposed in bore 211 so as to allow reciprocating movement of tube 215 within housing 210. Plunger mechanism 130 may be adapted for connection to gas tubing for gas flow into the plunger head 220 at inlet 221. The gas channel 216 of tube 215 is integrally connected to gas inlet 221 in plunger head 220 by a side bore or a straight bore (not shown). Tube 215 has the dual functions of (1) accepting gas flow via gas channel 216 from inlet 221 and conveying the gas to a sample tube 101, and (2) acting as a push rod for pushing a sample tube 101 from the sample tube manipulator 110.

FIG. 3A also shows the details of three sealing mechanisms 230, 235, 260 for preventing gas leakage during the desorption and measurement process. In one embodiment, manipulator 110 has a lower retainer/sealing mechanism 230 attached at the lower end thereof. In a preferred embodiment sealing mechanism 230 comprises an O-ring 231 and swadgelock fitting 232. Alternative seals useful in the invention are known to those skilled in the art. An upper sealing mechanism 235 is used to seal off possible gas flow between the outside of tube 215 and bore 211 of manipulator 110. If needed the central bore may be enlarged as needed to accommodate upper sealing mechanism 235. Preferably the upper sealing mechanism 235 is an O-ring. The upper sealing mechanism 235 may be located anywhere along the retracted length of tube 215 (up position) within the bore of manipulator 110. Alternative seals for upper sealing mechanism 235 are known to those skilled in the art. These may include compress fittings, a pliable ferrule and back ferrule assembly, among others. A third sealing mechanism 260 is located at the heater 150 and elbow 155 and is further discussed below.

In a preferred embodiment, manipulator 110 has a holding mechanism 240 for holding sample tubes 101. Holding mechanism 240 is typically attached at the lower end of manipulator 110. A presently preferred form for the holding mechanism includes an L-shaped tongue 241 having a hole 242 through its lower end, through which sample tubes 101 can pass. Tongue 241 is rotatively attached to housing 210 by pins 243. Pin 243 is inserted in holes in housing 110 and tongue 241 to rotatively engage tabs 244 located on the tongue 241. Spring 245 provides bias to maintain the tongue 241 in a position where it will not contact the walls of a sample tube inserted through hole 242. Tube 101 is held somewhat by frictional forces between the O-ring 231 and the sample tube 101; however, when the finger pad 247 is depressed and the tongue 241 rotates on pin 243 a firmer grip of sample tube 101 is obtained since tube 101 is then also held in place by frictional forces between the tongue 241 tube 101. Alternate means of holding the sample tube 101 are known in the art and may be used if desired. As noted above, in its normal position, the edge of hole 242 through which the sample tube 101 passes in the L-shaped lever 241 is not in contact with sample tube 101.

Alternate means for holding the sample tube (not shown) can include shaping hole 242 so as to maintain tongue 241 in frictional contact with sample tube 101. The sample tube is then always held firmly the friction of sealing mechanisms 230 and frictional forces from contact with the edge of hole 242. Bias spring 245 serves to provide pressure for maintaining the frictional forces until the holding mechanism 240 is depressed by finger action.

As mentioned above the plunger serves to push the sample tube 101 from the manipulator 110. After expulsion of the tube, plunger mechanism 130 is returned to a starting position after depression thereof by bias mechanism 250. In one embodiment bias mechanism 250 comprises a spring-loaded bias mechanism. Spring 251 is activated and held in place by retainer ring 254. Retainer plate 252 (that typically is held in place by screws 253 or other attachment such as rivets or adhesive) serves to stop the upward movement of retainer ring 254. The bore 211 of housing 210 may be enlarged at bias mechanism 250 to allow insertion and movement of retainer ring 254 and spring 251. Retainer ring 254 is immovably attached to tube 215 by welding, adhesive or other attachment means or is an integral formed part of tube 215. When plunger head 220 is depressed to eject a sample tube 101, retainer ring 254 moves downward with tube 215 and compresses spring 251. Upon release of plunger head 220, spring 251 pushes up on retainer ring 254 and pushes the plunger head 220 and tube 215 back up in preparation for receiving a new sample tube 101.

When a sample tube 101, containing analytes, is picked up for measurement with manipulator 110, the sample tube 101 is inserted into the heating block 150 where a third sealing mechanism is used in conjunction with elbow 155. One embodiment of the third sealing mechanism 260 may use an O-ring 261 swagelok combination as in the manipulator 110 that is mounted to the inlet end of elbow 155 (gas receiving mechanism). After the sorbed materials are heated in the heating area for a set period of time (at a temperature where the analytes are released from the sorbent and enough time has elapsed to at least substantially release the analytes), an on/off valve 205 between the heating block 150 and the measuring device (e.g. a mass spectrometer or a mass chromatograph with an appropriate detector such as a flame ionization detector, and the like) is opened and a "plug" of sample is introduced into the measuring device 190. After analysis, the valves are closed and the sample tube 101 is removed from the heating block 150. Temperature of the heating block may be monitored with thermocouple 134. The lower end of sample tube 101 makes contact with sealing mechanism 260 at O-ring 261.

Figure 3B:
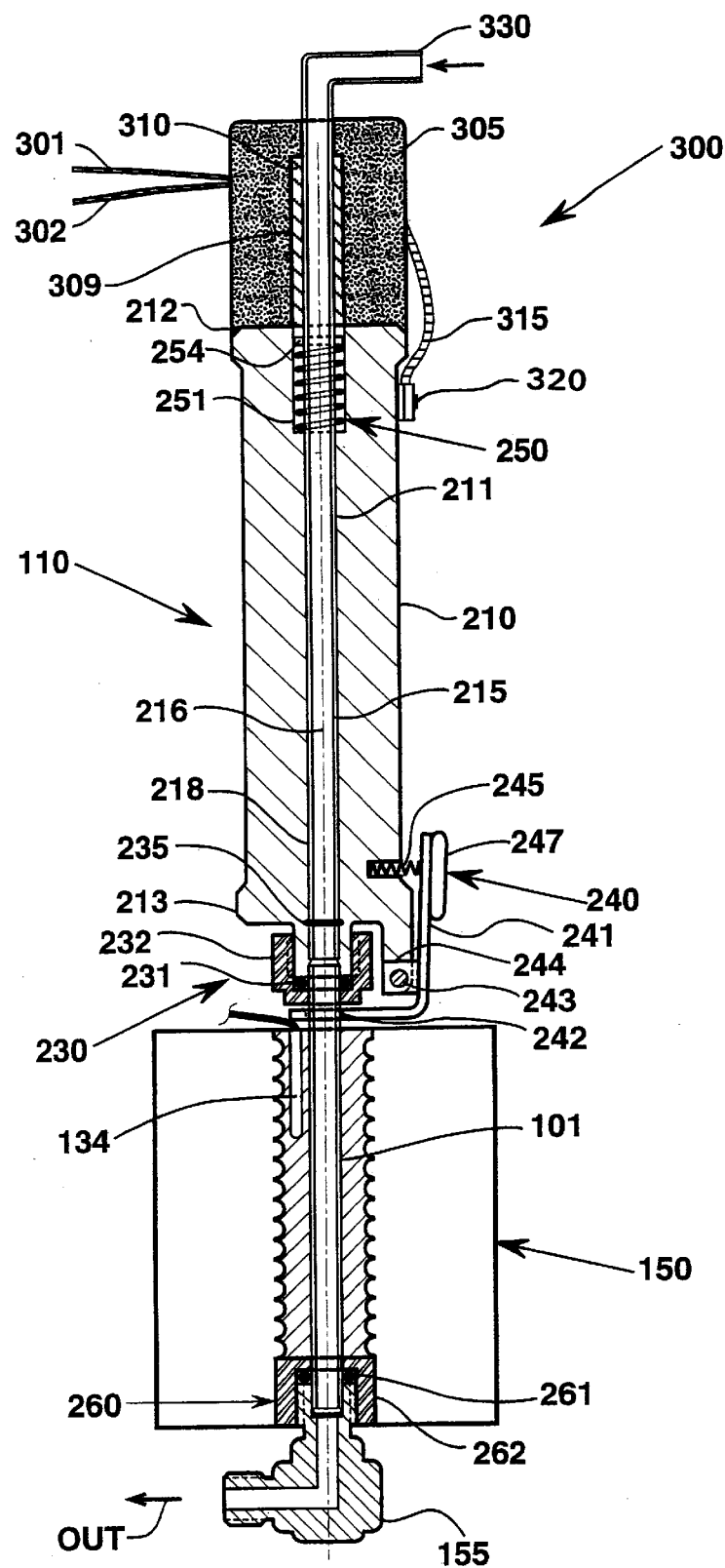
FIG. 3B is a cutaway view of the hand held sample tube manipulator 110 configured so as to expel a sample tube 101 by use of a solenoid operated mechanism that replaces plunger mechanism 130.
Figure 3C:
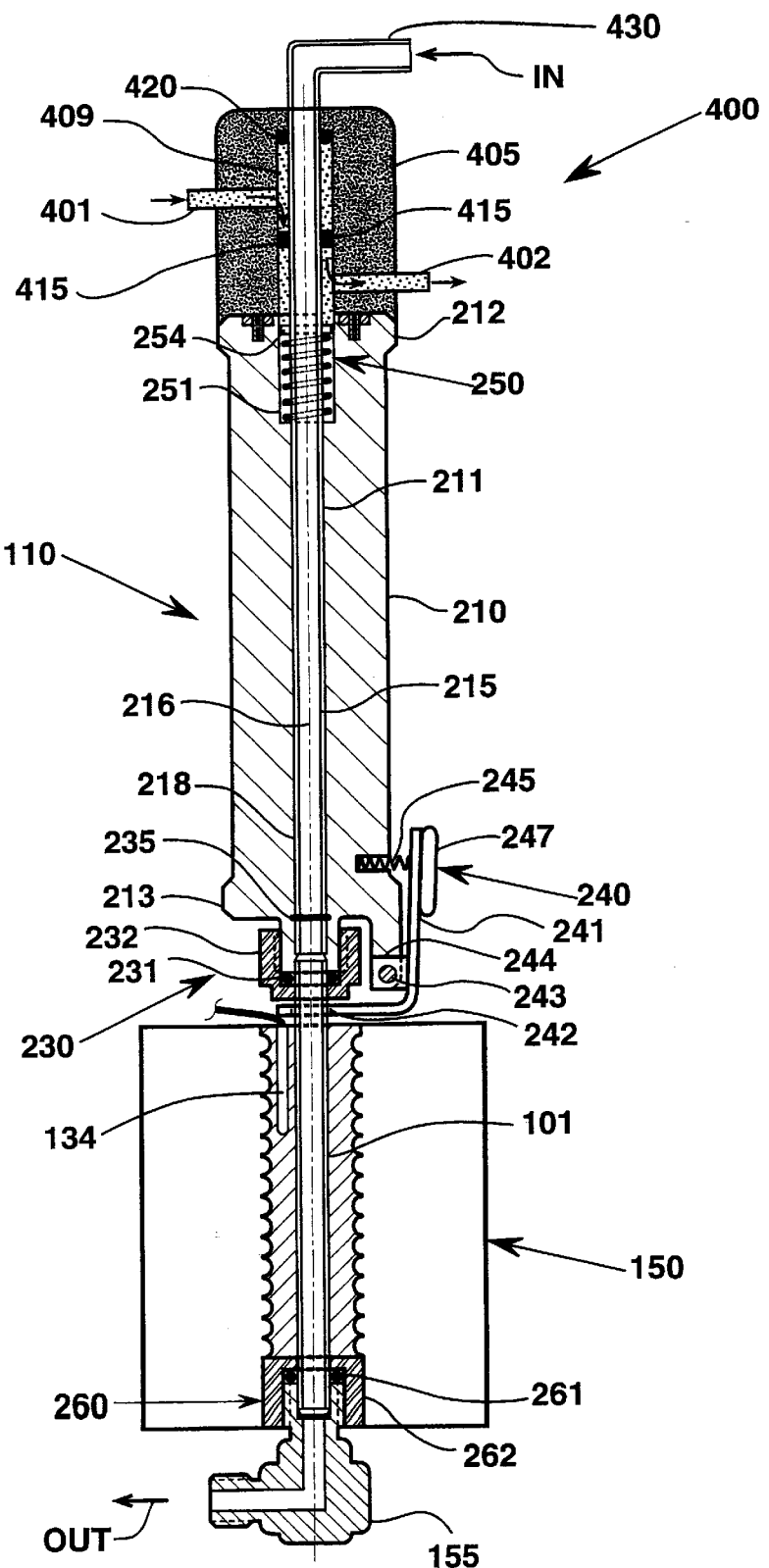
FIG. 3C is a cutaway view of the hand held sample tube manipulator 110 configured so as to expel a sample tube 101 by use of a pressurized air operated mechanism that replaces plunger mechanism 130.

Referring now to FIG. 3B, this figure shows details of an alternate embodiment for actuation of plunger mechanism 130. Reciprocal movement of tube 215 is achieved with a solenoid mechanism 300 connected to a source of electrical power by electrical leads 301, 302 that supply power to solenoid windings 305. Solenoid windings 305 are arranged in known ways to provide a magnetic field that moves a metal core 310 located within chamber 309 downward. Metal core 310 is attached to tube 215 by welds, glue, fasteners and the like. When activated by an electrical field, movement of metal core 310 impels tube 215 downward and expels sample tube 101.

Solenoid 305 is controlled through leads 315 by depression of actuator button 320 that is mounted on housing 210. When actuator button 320 is depressed the electrical circuit is closed and current flows through the solenoid windings 305. Metal core 310 and sample tube 215 are be returned to their starting position by biasing means such as spring mechanism 250. If desired, return of the core 310 and tube 215 can be augmented by the solenoid powered so as to return the core and tube 215 to the starting position. Alternatively, the solenoid can act alone. The solenoid mechanism 300 is shown held in place by screws 253 but can be attached to housing 210 by glue, rivets and other known means. The upper end of tube 215 may be bent as shown into tube 330 and may be adapted for attachment to an air supply or a vacuum.

Referring now to FIG. 3C, this figure shows details of an embodiment that provides for an air actuated and powered plunger means for movement of tube 215. Reciprocal movement of tube 215 is achieved with pneumatic actuator 400 that is powered by pressurized air flowing into inlet 401. Excess air within chamber 409 is exited at outlet 402. A piston 415 attached to tube 215 moves down in response to the pressurized air entering at inlet 401. Chamber 409 is sealed at the upper end by seal 420. Control of air flow to pneumatic actuator 400 may be remote as with a foot pedal (not shown) or may be local with a control switch (not shown) mounted to the housing 210 as is the case with the actuator button in FIG. 3B. Tube 215 and piston 415 may be returned to their upper starting position by spring mechanism 250. If desired, return of tube 215 to its starting position may be augmented by reversal or air pressure or alternatively the pneumatic actuator 400 may act alone. The pneumatic actuator 400 is shown held in place by screws 253 but can be attached to housing 210 by glue, rivets and other known means. The upper end of tube 215 may be bent as shown into tube 430 and may be adapted for attachment to an air supply or a vacuum.

If desired the thumb actuated plunger head 220 may be retained in embodiments using both electrical and pneumatic actuation for ejection of sample tube 215. Other means for providing reciprocal movement of tube 215 include small motors and levers.

Test and Results

The chemical sensor was tested using Tenax™ sample tubes as the sample tubes 101. The sample tubes 101 were spiked with varying known amounts of carbon tetrachloride ($CCl_4$). A gas cylinder containing a known concentration of $CCl_4$ was diluted and a known volume of gas was passed through the sampling tube 101. The total mass (in nanograms) of $CCl_4$ on the sampling tubes was then calculated.

The first calibration/sensitivity tests were performed using a Finnigan Ion Trap Mass Spectrometer (ITMS) System (San Jose, Calif.) equipped with an Atmospheric Sampling Glow Discharge Ionization source (ASGDI) (Oak Ridge National Laboratory, Oak Ridge, Tenn.), and the Teledyne HST-1000™ Accessory Kit (Teledyne, Mountainview, Calif.). The Accessory Kit allows the ITMS to use the Filtered Noise Field operating mode developed by Teledyne MEC (Mountainview, Calif.). All analyses were performed in the MS/MS mode isolating the parent ion of m/z 117 (M-Cl), then dissociating it to the daughter ion of m/z 82. All sample tubes 120 were cleaned (heated to 275° C. and purged with ultra high purity helium at 50 cc/min for 0.5 hours) before use. A cleaned empty tube (without sorbent), a cleaned blank tube (containing sorbent) and cleaned tubes with sorbent with several spiked samples ranging from 6 nanograms (ng) to 881 ng were analyzed.

As mentioned above, the sample tube 101 was secured to the bottom of the manipulator 110, a flow of helium was started to purge the residual air out of the sample tube 101. (Excess oxygen in the tube 101 during heating can degrade the analytes of interest that are adsorbed on the sorbent.) The tube 101 was placed in the heating block 150 (heated at 250° C.) for two minutes. At the end of the heating period, the on/off valve 204 between the heating block 150 and the measuring device, in this case an ion source mass spectrometer was opened and the "plug" of sample was introduced into the mass spectrometer. The valves were closed after the analysis and the tube 101 was removed from the heating block 150 and ejected from the sample tube manipulator 110 by depressing the plunger head 220 on the housing 210. The ITMS air-sampling rate was 195 mL/min, and desorption gas flow rate was 70 mL/min.

Figure 4:
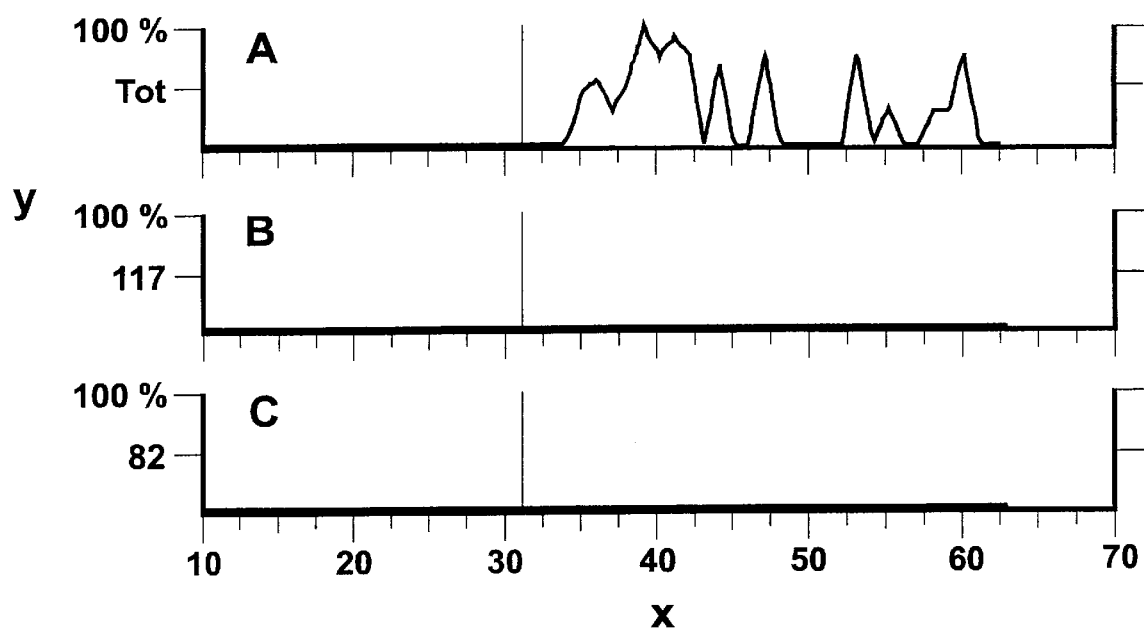
FIG. 4A is a total ion chromatogram from analysis of a totally empty sorbent tube (typical of the sample tubes used herein) and shows the trace amounts of chemicals present.
FIGS. 4B and 4C are parent (m/z 117) and daughter (m/z 82) ion chromatograms, respectively, from analysis of a totally empty sorbent tube. The vertical scales (Y) are in arbitrary units representing intensity where 100% equals 19 units. The horizontal scale (X) is in units of time where each unit is equal to 3.3 seconds.
Figure 5:
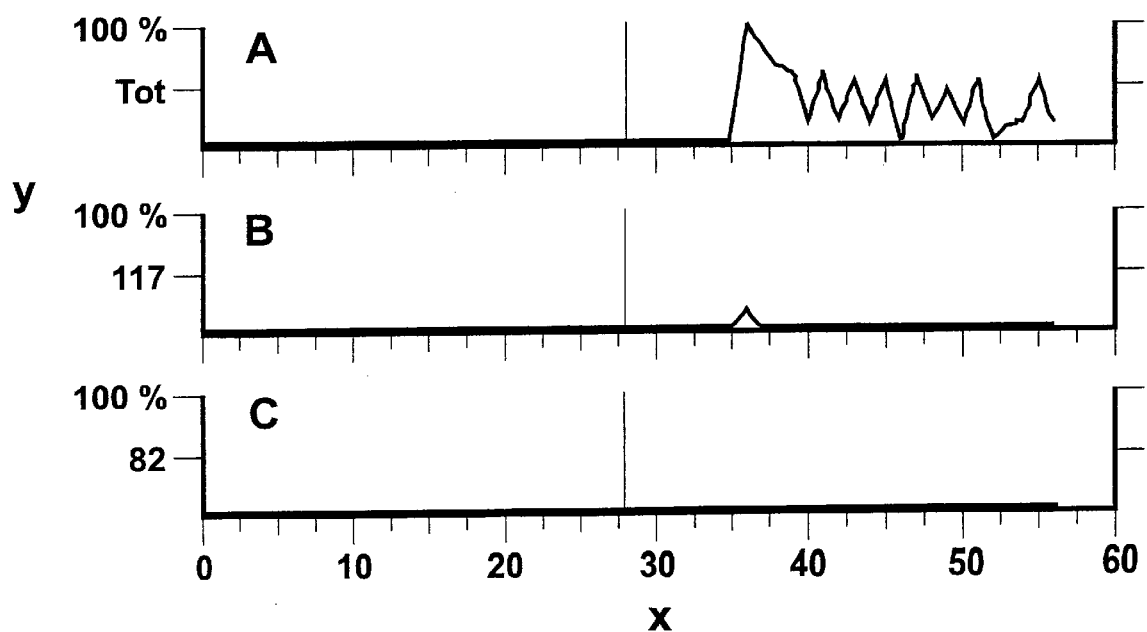
FIG. 5A is a total ion chromatogram from analysis of a blank sorbent tube (empty tube plus sorbent) and shows the trace amounts of chemicals present.
FIGS. 5B and 5C are parent and daughter ion chromatograms, respectively, from analysis of the blank sorbent tube. The vertical scales (Y) are in arbitrary units representing intensity where 100% equals 39 units. The horizontal scale (X) is in units of time where each unit is equal to 3.3 seconds.
Figure 6:
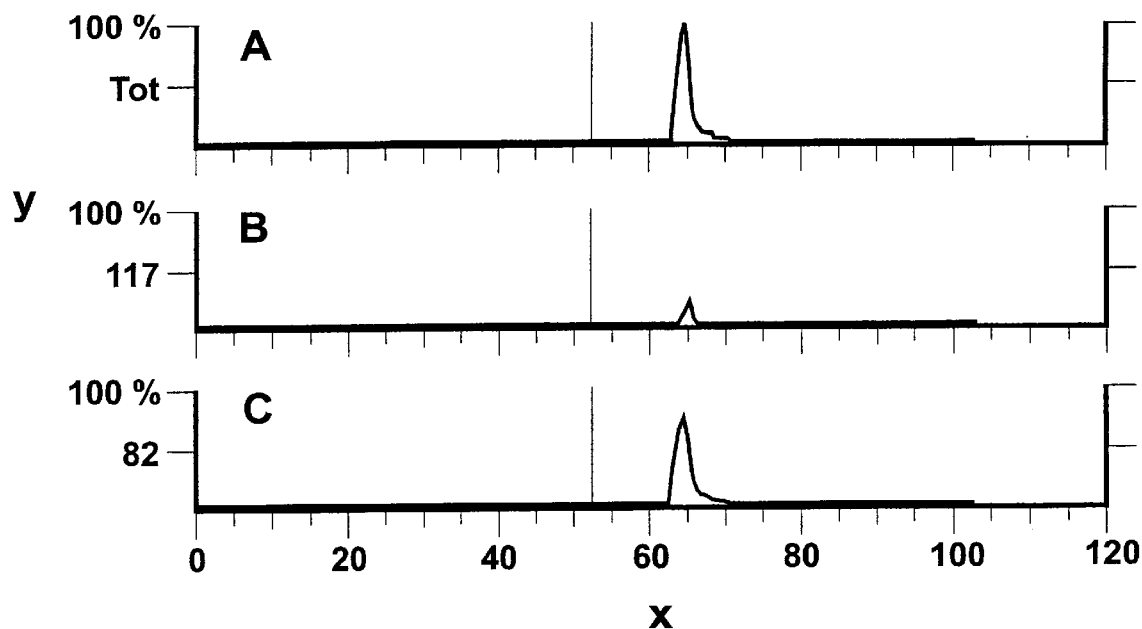
FIG. 6A is a total ion chromatogram from analysis of a sorbent tube spiked with 882 ng of $CCl_4$.
FIGS. 6B and 6C are parent and daughter ion chromatograms, respectively, from analysis of the spiked sorbent tube. The vertical scales (Y) are in arbitrary units representing intensity where 100% equals 11,753 units. The horizontal scale (X) is in units of time where each unit equals 3.3 seconds.
Figure 7:
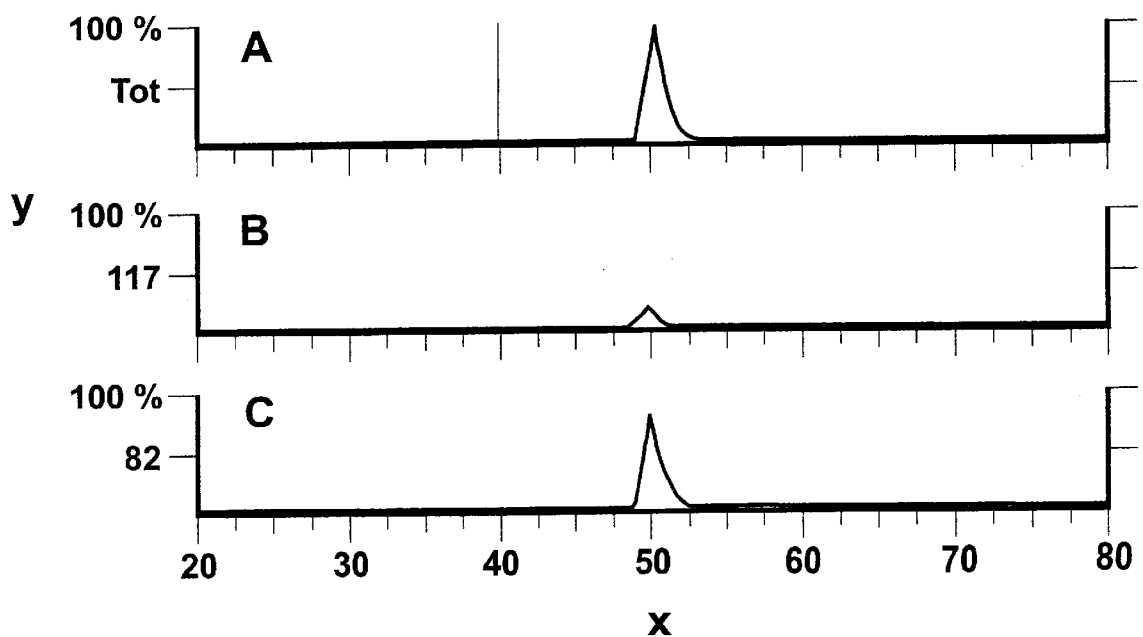
FIG. 7A is a total ion chromatogram from analysis of a sorbent tube spiked with 441 ng of $CCl_4$.
FIGS. 7B and 7C are parent and daughter ion chromatograms, respectively, from analysis of the spiked sorbent tube. The vertical scales (Y) are in arbitrary units representing intensity where 100% equals 8,202 units. The horizontal scale (X) is in units of time where each unit equals 3.3 seconds.
Figure 8:
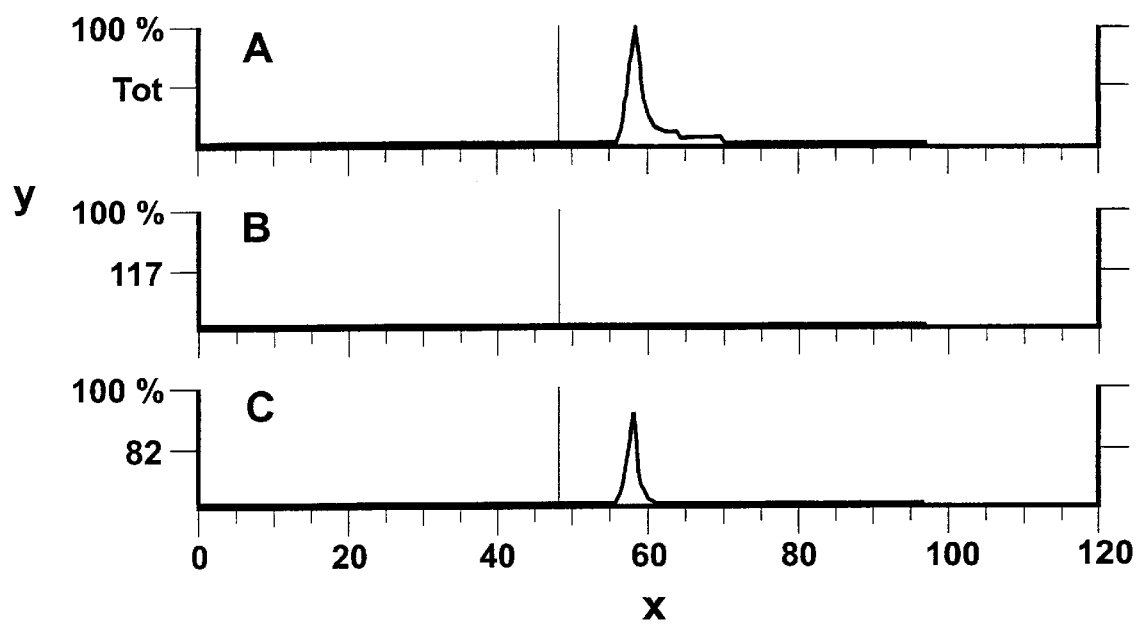
FIG. 8A is a total ion chromatogram from analysis of a sorbent tube spiked with 50 ng of $CCl_4$.
FIGS. 8B and 8C are parent and daughter ion chromatograms, respectively, from analysis of the spiked sorbent tube. The vertical scales (Y) are in arbitrary units representing intensity where 100% equals 819 units. The horizontal scale (X) is in units of time where each unit equals 3.3 seconds.
Figure 9:
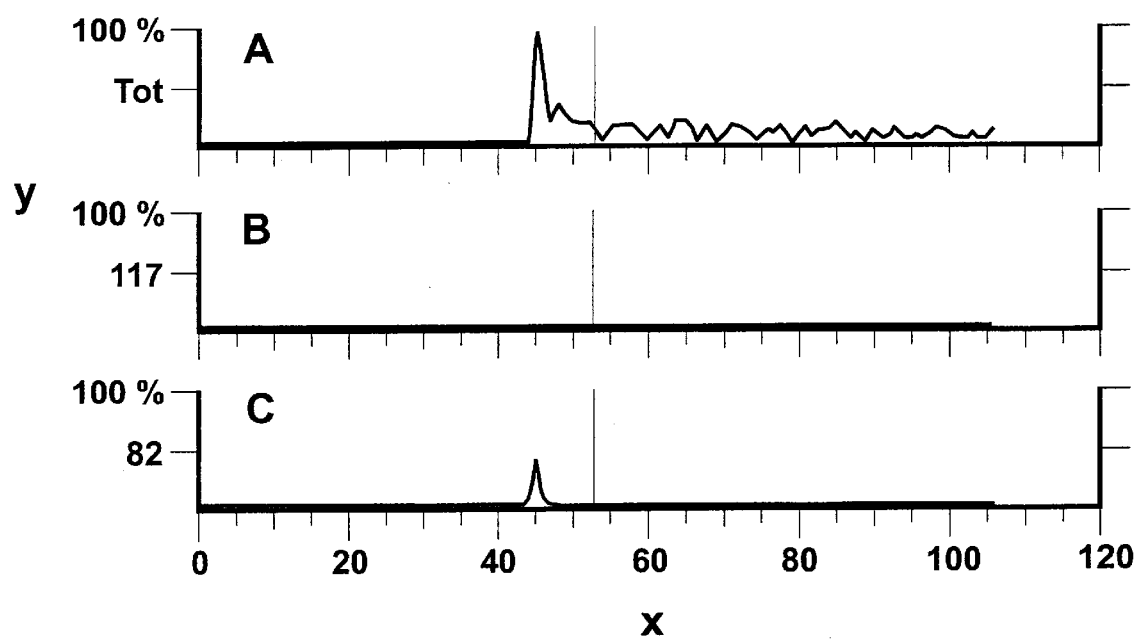
FIG. 9A is a total ion chromatogram from analysis of a sorbent tube spiked with 6 ng of $CCl_4$.
FIGS. 9B and 9C are parent and daughter ion chromatograms, respectively, from analysis of the spiked sorbent tube. The vertical scales (Y) are in arbitrary units representing intensity where 100% equals 165. The horizontal scale (X) is in units of time where each unit equals 3.3 seconds.

Referring now to FIGS. 4 to 10, these figures show ion chromatograms obtained from measurement of sample tubes containing varying amounts of $CCl_4$ and the signals from this series of tests. FIGS. 4 and 5 show the ion chromatograms from the empty tube and blank sample tube tests respectively. The lack of any response at m/z 82 illustrates that there is no background contamination from the $CCl_4$.

The sample tubes 101 used for development of the chromatograms for FIGS. 6 through 10 were spiked with varying amounts of $CCl_4$ to simulate various loadings of this chemical in a sample tube. FIG. 6A shows the total ion chromatogram from analysis of the response from an 882 ng spike where 100% (y-axis) represents 11753 arbitrary units of intensity. FIG. 7A shows the total response from a 441 ng spike, FIG. 8A shows the total response from a 50 ng spike, and FIG. 9A shows the total response for a 6 ng spike.

Figure 10:
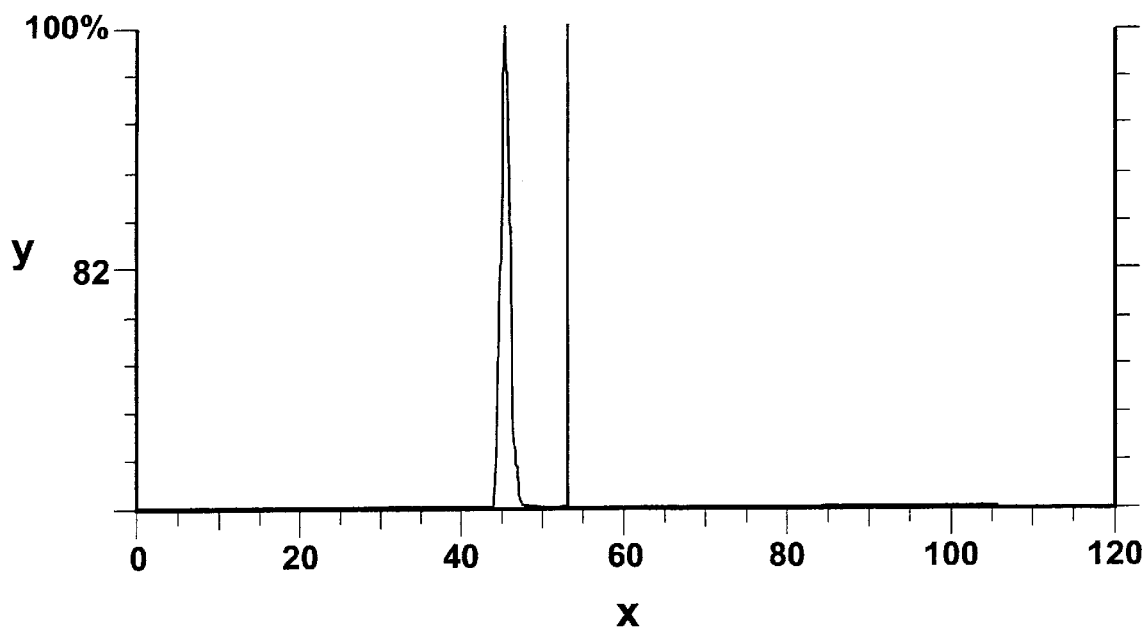
FIG. 10 is a selected ion chromatogram of daughter ion m/z 82 from analysis of a sorbent tube spiked with 6 ng of $CCl_4$. The vertical scale (Y) is in arbitrary units representing intensity where 100% equals 71 units. The horizontal scale (X) is in units of time where each unit equals 3.3 seconds.

FIG. 10 shows only the selected ion chromatogram for m/z 82 of $CCl_4$ from a 6 ng spiked tube. Detection limits are on the order of 1–2 ng of $CCl_4$ on the sample desorption tube. FIG. 10 is a blowup of the daughter ion response to show the signal to noise ratio. The figure demonstrates a very good signal to noise ratio and that one can go lower on the detection limit.

Figure 11:
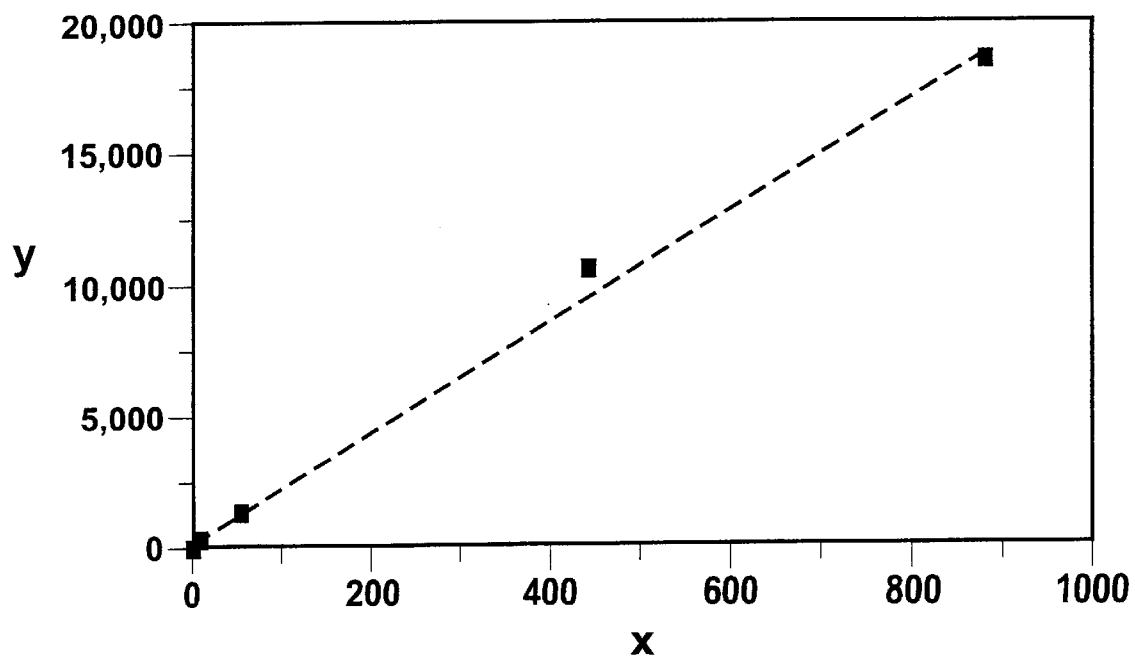
FIG. 11 is a calibration curve generated from sample tube analysis. The vertical scale (Y) represents peak areas and the horizontal scale (X) represents the amount spiked into the sorbent tube in nanograms.

FIG. 11 shows the calibration curve generated from the spiked sample tubes.

The Table below shows the peak areas and peak heights from the spiked sample tubes. The Table also shows the linear regression data from the calibration curve. These data were used to generate the calibration curve of FIG. 11.

TABLE

Summary of peak area and peak heights from sample tubes spiked with $CCl_4$

| $CCl_4$ Spiked on Tube (ng) | Peak Area | Peak Height | Response Factor (Area) | Response Factor (Height) |
|---|---|---|---|---|
| 882 | 18583 | 7153 | 21 | 8.1 |
| 441 | 10676 | 6299 | 24 | 14 |
| 50 | 1084 | 643 | 22 | 13 |
| 6 | 83 | 71 | 14 | 12 |
| Average RF | | | 20 ± 4 | 12 ± 3 |

Under normal conditions air samples for the sample tubes 120 are collected at a rate of 5–10 cc/min. This means that at a flow rate of 10 cc/min a total of 4.8 liters of air are collected over an 8 hour period. With an instruction detection limit of 2 ng this correlates to a method detection limit of 0.42 ng/L collected. For carbon tetrachloride 6.22 ng/liter equals 1.0 ppbv (MW/22.4 liter/Mole). Therefore, the detection limit for the ambient air concentration is 0.06 ppbv.

The sensitivity tests using the ITMS/HST-1000™ system show that the hand held sample tube manipulator and associated system can be successfully deployed as a chemical sensor subsystem of an exhaled air and/or environmental air monitoring and analysis system.

Optimization of the heating times and desorption flow rates has not been performed but can be readily made by those skilled in the art using the disclosure herein.

Although the ITMS is a laboratory-based system and will not be the mass spectrometer used as part of a breath/exposure monitor, other mass spectrometers known to those skilled in the art may be used for a portable system (e.g. Teledyne 3DQ™, and Teledyne Discovery 2™. The ITMS was used as a "benchmark". The ITMS has been used for many ambient air analysis applications and is typical of laboratory based mass spectrometers that can be used. Other laboratory based mass spectrometers can be used as is known by those skilled in the art (e.g. Finnigan TSQ™, Finnigan LCMS™).

At the present time, the sample tube manipulator 110 can be successfully used as part of a field deployed breath/exposure monitoring system. Minor design modifications within the ordinary skill of the artisan are envisioned to make the system better. All of the valving for the gas flow described above is presently performed manually; however, computer controlled solenoid valves and flow controllers can be substituted for the manual valves and flow metering valves. For a computer-controlled system, control mechanisms 125, 160, vacuum pump 295, and optionally heater 150 would all have wiring known in the art for connection to the computer (not shown). These interconnections are well known and are easily made by those skilled in the art.

An alternate embodiment, not shown, where the holding mechanism is permanently biased to hold the sample tube 101 unless released, provides for a coupled action of the depression of the plunger head and release of the holding mechanism. This embodiment can easily be adopted by those skilled in the art.

While the forms of the invention herein disclosed constitute presently preferred embodiments, many others are possible. It is not intended herein to mention all of the possible equivalent forms or ramifications of the invention. It is to be understood that the terms used herein are merely descriptive, rather than limiting, and that various changes may be made without departing from the spirit of the scope of the invention.

We claim:

1. A sample tube manipulator comprising:
   a. housing means having a central bore with an inlet end and outlet end;
   b. plunger means at least a portion of which is slideably disposed within said central bore, for reciprocal movement therein, for expelling a sample tube inserted in said bore at said outlet end of said housing means, having a gas channel with an inlet end and an outlet end, said gas channel inlet end disposed in the same direction as said inlet end of said central bore, said inlet end of said movable plunger means adapted for connection to gas supply means;
   c. first sealing means disposed in said housing means adapted for sealing between said central bore and said moveable plunger means;
   d. second sealing means disposed at the outlet of said housing means adapted for sealing between said central bore and an inserted sample tube;
   e. holding means mounted on said housing means adapted to hold said sample tube while allowing ejection of said sample tubes when said plunger means moves reciprocally; and
   f. biasing means for returning said plunger means to a starting position after movement of said plunger means.

2. The sample tube manipulator according to claim 1, wherein said plunger means comprises a plunger head adapted for manual depression.

3. The sample tube manipulator according to claim 1, wherein said plunger means comprises a solenoid means.

4. The sample tube manipulator according to claim 1, wherein said plunger means comprises a pneumatic means.

5. The sample tube manipulator according to claim 1, wherein said plunger means comprises said reciprocally moveable portion and a stationary portion disposed on said housing means for powering said reciprocally moveable portion.

6. The sample tube manipulator according to claim 5, wherein said stationary portion comprises a portion of a glove.

7. A method for measuring analytes present in a sample tube comprising:
   a. inserting one end of said sample tube in the sample tube manipulator of claim 1 and moving said sample tube;
   b. mating said sample tube with a gas sealing and receiving means adapted to seal the other end of said sample tube from the environment;
   c. heating said sample tube in a manner adapted to desorb analytes present in said sample tube;
   d. providing a flow of gas to sweep said analytes from said sample tube; and
   e. directing said gas flow from said gas sealing and receiving means to a measuring device and measuring for the presence of selected analytes.

8. The system of claim 7 wherein said measuring device comprises a mass spectrometer or a gas chromatograph.

9. A sample tube manipulator comprising:
   a. a housing having a central bore having an upper and a lower end;
   b. a plunger mechanism having a tubular portion slideably disposed in the upper end of said bore for reciprocal movement in said bore, said plunger mechanism having a gas channel between upper and lower ends, the upper end of said plunger mechanism adapted to power said plunger mechanism, the lower end of said tubular portion of said plunger mechanism adapted to mate with a sample tube inserted in said lower central bore end for providing gas flow from said gas channel to said sample tube, said plunger mechanism adapted to expel a sample tube inserted in the lower end of said central bore when said plunger mechanism moves;
   c. a first gas seal disposed in said central bore, between said bore and said tubular portion of said plunger, providing gas sealing in the space between said tubular portion of said plunger mechanism and said central bore;
   d. a second gas seal disposed at the lower portion of said housing, providing gas sealing around the outer circumference of an inserted sample tube;
   e. a tube holder disposed at the lower portion of said housing, adapted to hold a sample tube inserted in the lower portion of said housing; and
   f. a biasing mechanism disposed at the upper end of said housing adapted to return said plunger mechanism to a starting position after movement of said plunger mechanism.

10. The sample tube manipulator according to claim 9, wherein said plunger mechanism comprises a plunger head adapted for manual depression.

11. The sample tube manipulator according to claim 9, wherein said plunger mechanism comprises a solenoid mechanism.

12. The sample tube manipulator according to claim 9, wherein said plunger mechanism means comprises a pneumatic mechanism.

13. The sample tube manipulator according to claim 9, wherein said plunger mechanism comprises said reciprocally moveable portion and a stationary portion disposed on said housing for powering said reciprocally moveable portion.

14. The sample tube manipulator according to claim 13, wherein said stationary portion comprises a portion of a glove.

15. A method for measuring analytes present in a sample tube comprising:
   a. inserting one end of said sample tube in the sample tube manipulator of claim 9 and moving said sample tube;
   b. mating said sample tube with a gas sealing and receiving means adapted to seal the other end of said sample tube from the environment;
   c. heating said sample tube in a manner adapted to desorb analytes present in said sample tube;
   d. providing a flow of gas to sweep said analytes from said sample tube; and
   e. directing said gas flow from said gas sealing and receiving means to a measuring device and measuring for the presence of selected analytes.

16. The system of claim 15 wherein said measuring device comprises a mass spectrometer or a gas chromatograph.

* * * * *

UNITED STATES PATENT AND TRADEMARK OFFICE
CERTIFICATE OF CORRECTION

PATENT NO.   : 6,186,012 B1                                         Page 1 of 1
DATED         : February 13, 2001
INVENTOR(S) : Donald V. Kenny, Deborah L. Smith, Richard A. Severance It is certified that error appears in the above-identified patent and that said Letters Patent is hereby corrected as shown below:

<u>Column 6,</u>
Line 63, "20A" should be -- 205 --

Signed and Sealed this

Nineteenth Day of February, 2002

Attest:

*Attesting Officer*

JAMES E. ROGAN
*Director of the United States Patent and Trademark Office*